(12) United States Patent
Satou et al.

(10) Patent No.: US 11,339,133 B2
(45) Date of Patent: May 24, 2022

(54) METHOD FOR PRODUCING TRIAZOLIDINEDIONE COMPOUND

(71) Applicants: TOKUYAMA CORPORATION, Yamaguchi (JP); JEOL Ltd., Tokyo (JP)

(72) Inventors: Makoto Satou, Yamaguchi (JP); Misao Matsushige, Yamaguchi (JP); Seketsu Fukuzawa, Tokyo (JP); Masaki Takiwaki, Tokyo (JP)

(73) Assignees: TOKUYAMA CORPORATION, Yamaguchi (JP); JOEL LTD., Tokyo (JP)

( * ) Notice: Subject to any disclaimer, the term of this patent is extended or adjusted under 35 U.S.C. 154(b) by 0 days.

(21) Appl. No.: 16/973,216

(22) PCT Filed: Jun. 11, 2019

(86) PCT No.: PCT/JP2019/023165
§ 371 (c)(1),
(2) Date: Dec. 8, 2020

(87) PCT Pub. No.: WO2019/240142
PCT Pub. Date: Dec. 19, 2019

(65) Prior Publication Data
US 2021/0253541 A1 Aug. 19, 2021

(30) Foreign Application Priority Data

Jun. 12, 2018 (JP) .............................. JP2018-112194

(51) Int. Cl.
*C07D 249/12* (2006.01)
(52) U.S. Cl.
CPC .................. *C07D 249/12* (2013.01)
(58) Field of Classification Search
CPC ................................................ C07D 249/12
See application file for complete search history.

(56) References Cited

U.S. PATENT DOCUMENTS

| 4,386,213 A | 5/1983 | Giesecke et al. |
| 2018/0088137 A1 | 3/2018 | Higashi et al. |

FOREIGN PATENT DOCUMENTS

| JP | S57-050974 A | 3/1982 |
| JP | 2018-054459 A | 4/2018 |
| WO | 2013-009564 A1 | 1/2013 |

OTHER PUBLICATIONS

S. Mallakpour, et al., Journal of Applied Polymer Science, 2007, vol. 103, pp. 947-954.
S. Ogawa, et al., Rapid Commun. Mass Spectrom., 2013, vol. 27, 00. 2453-2460.
S. Mallakpour, et al., Polymer Bulletin, 2006, vol. 56, pp. 293-303.
Shoghi Elham et al., "Solubility-pH Profiles of Some Acidic, Basic and Amphoteric Drugs," European Journal of Pharmaceutical Sciences, Elsevier Amsterdam, NL, vol. 48, No. 1, Nov. 22, 2012 (Nov. 22, 2012), pp. 291-300, XP028975336, ISSN:0928-0987, DOI:10:1016/J.EJPS.2012.10.028.

*Primary Examiner* — Shawquia Jackson
(74) *Attorney, Agent, or Firm* — Hogan Lovells US LLP

(57) ABSTRACT

Provided is a method for industrially producing a triazolidinedione compound at a high purity and a high yield. A precipitation step for preparing a solution that contains a triazolidinedione compound represented by formula (1) and precipitating the triazolidinedione compound therefrom is performed. In this step, the pH of the solution is adjusted to 3.0 to 8.5 and the solution is prepared so as to contain 3-15 parts by volume of solvents for 1 part by mass of the triazolidinedione compound. (In the formula, $R^1$ is a substituted or unsubstituted amino group-bearing organic group.)

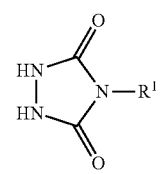

(1)

1 Claim, No Drawings

METHOD FOR PRODUCING TRIAZOLIDINEDIONE COMPOUND

This application is a U.S. National Phase under 35 U.S.C. § 371 of International Application PCT/JP2019/023165 filed on Jun. 11, 2019, which are incorporated herein in their entirety. This application also claims priority to Japanese Patent Application No. 2018-112194, filed on Jun. 12, 2018. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a method for producing a triazolidinedione compound.

BACKGROUND ART

Metabolome analysis, which comprehensively analyzes metabolites, has recently attracted attention. The metabolome analysis refers to a method of analyzing a sample by mass spectrometry, nuclear magnetic resonance, and the like, and analyzing the obtained data, and is utilized for e.g. developments in the fields of pharmaceuticals and food products. However, with regard to the mass spectrometry, a target compound may have low detection sensitivity. As a countermeasure, a method in which the target compound is derivatized to increase its sensitivity is performed.

A target compound having low detection sensitivity for the mass spectrometry is exemplified by 25-hydroxyvitamin $D_3$. The 25-hydroxyvitamin $D_3$ is one of vitamin D metabolites that is essential for biological activities, and in the case of a deficiency in the vitamin D, rickets, osteoporosis and the like will develop. Therefore, tracing of the vitamin D and the Vitamin D metabolites thereof is considered to be very useful for detection and prevention of diseases.

However, any technology for accurately tracing a steroid compound such as vitamin D in vivo is not yet established, and the steroid compound is currently analyzed by way of derivatization thereof with a reagent to increase the sensitivity. Specifically, the vitamin D is derivatized using a Cookson-type reagent as a derivatization reagent, before the Vitamin D is detected by mass spectrometry (see Nonpatent Document 1).

Here, among Cookson reagents, 4-(dimethylaminophenyl)-1,2,4-triazoline-3,5-dione (hereinafter, abbreviated as DAPTAD) represented by the following structural formula (9) is a compound that is highly reactive, rapidly causes Diels-Alder reaction with a conjugated diene, and therefore can be beneficially utilized for derivatization of vitamin D in the blood, and the like.

In addition, Nonpatent Document 2 discloses the following synthetic route as a production method of DAPTAD. More specifically, carboxylic acid (3) is converted to acyl azide (4) using diphenylphosphoryl azide, and the acyl azide (4) is subjected to Curtius rearrangement to thereby obtain isocyanate (5). Then, the obtained isocyanate (5) is reacted with hydrazine derivative (6) to obtain semicarbazide (7), and the obtained semicarbazide (7) is cyclized under basic conditions to thereby form triazolidinedione compound (8). Then, the triazolidinedione compound (8) is subjected to an oxidation reaction to obtain DAPTAD (9).

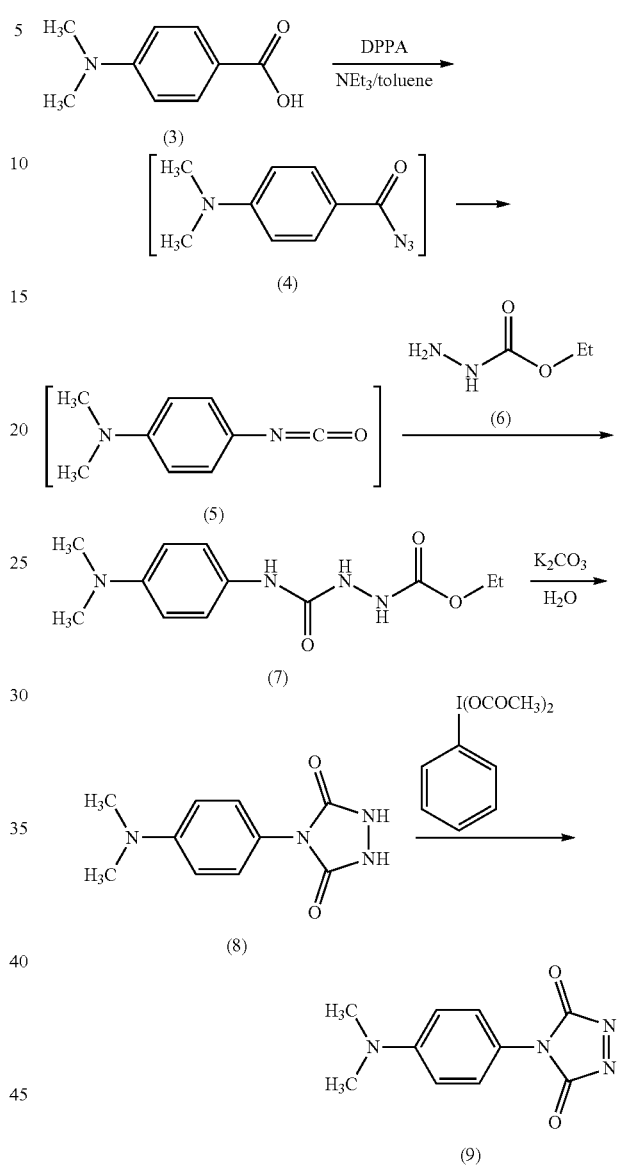

While compounds having a 1,2,4-triazoline-3,5-dione structure, which are typified by DAPTAD, exhibit very high reactivity with diene compounds, such compounds are very unstable. In other words, the compounds themselves are extremely highly reactive, and readily decompose in most organic solvents. For this reason, the compounds need to be stored at low temperatures of −20° C. or lower under light shading, and are difficult to handle. For example, also in Nonpatent Document 1, DAPTAD is formed by oxidizing a triazolidinedione compound which is a precursor of DAPTAD with an oxidizing agent, and thereafter DAPTAD is directly reacted with vitamin D3 for utilization in metabolome analysis.

Therefore, a strategy in which the compounds having a 1,2,4-triazoline-3,5-dione structure, which are typified by DAPTAD, are handled not as triazolinedione compounds but as triazolidinedione compounds, which are precursors of the triazolinedione compounds, and oxidation reaction of the triazolinedione compounds is performed just before their utilization is considered to be promising.

Non-Patent Document 1: S. Mallakpour, et al., Journal of Applied Polymer Science, 103 (2) (2007) 947-954

Non-Patent Document 2: S. Ogawa, et al., Rapid Commun. Mass Spectrom, 27 (2013) 2453-2460

DISCLOSURE OF THE INVENTION

Problems to be Solved by the Invention

A method for producing a triazolidinedione compound, which is a precursor of a triazolinedione compound, is exemplified by a method in which semicarbazide is cyclized under basic conditions in ethanol into which sodium metal is added, then the reaction solution is neutralized (pH 6) with acetic acid to separate the triazolidinedione compound as crystals, and subsequently recrystallization is performed to isolate the triazolidinedione compound (see Nonpatent Document 1). However, this method is far from an industrial production method, since the method employs sodium metal. Moreover, Nonpatent Document 1 does not describe the purity of the crude crystals, yields after the recrystallization, and the purity of the isolated crystals.

Further, Nonpatent Document 2 describes that the cyclization reaction of semicarbazide is performed by heating the basic aqueous solution of the semicarbazide, the neutralization with acetic acid is performed, water is evaporated under reduced pressure, and thereafter purification by column chromatography on Wakogel (registered trademark) 100C18 is performed to obtain the triazolidinedione compound. However, this method is difficult to utilize industrially, since the purification by column chromatography is requisite for the method.

As mentioned above, the Cookson-type reagent such as DAPTAD is utilized for the metabolome analysis including the detection of vitamin D in the blood, and for fulfilling highly accurate measurements in mass spectrometry of vitamin D3 and the like, which are minor components, the Cookson-type reagent, which is a derivatization reagent, and furthermore the triazolidinedione compound, which is a precursor of the Cookson-type reagent, are required to have high purity.

The present invention has been made in view of the aforementioned necessity, and an object thereof is to provide a method for producing the triazolidinedione compound with high purity in high yields in an industrial manner.

Means for Solving the Problems

The present inventors conducted extensive studies for solving the aforementioned problems. Consequently, the present inventors found that in the synthesis of the semicarbazide compound according to the aforementioned synthetic route, by-products in the azidation reaction and/or impurities from the azidation agent are contained in the semicarbazide compound, and these compounds are water soluble under acidic to weakly alkaline conditions. Further, it was found that the semicarbazide compound forms the triazolidinedione compound via a cyclization reaction in the presence of a base, and the solubility of the triazolidinedione compound drastically varies depending on the pH of an aqueous solution.

Based on these findings, investigations were made on the pH of the triazolidinedione compound-containing aqueous solution obtained after the production of the triazolidinedione compound, and it was consequently found that adjustment of the pH so as to achieve acidic to weakly alkaline conditions enables a highly pure triazolidinedione compound to be obtained by an isoelectric point precipitation method, and thus the present invention was accomplished.

More specifically, the present invention relates to a method for producing a triazolidinedione compound, including a precipitation step of preparing a solution containing a triazolidinedione compound represented by the following formula (1), and precipitating the triazolidinedione compound, in which the pH of the solution is 3.0 to 8.5, and the solution contains a solvent in an amount of 3 to 15 parts by volume with respect to 1 part by mass of the triazolidinedione compound.

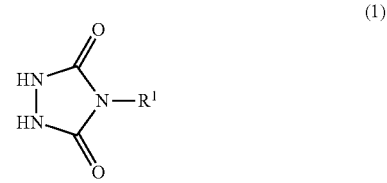

(1)

In the formula (1), $R^1$ represents an organic group including a substituted or unsubstituted amino group.

$R^1$ in the formula (1) may represent a substituted or unsubstituted aminoalkyl group having 1 to 6 carbon atoms, or a substituted or unsubstituted aminophenyl group or a substituted or unsubstituted aminoalkylphenyl group.

The method may include a cyclization step of reacting a semicarbazide compound represented by the following formula (2) with a base to obtain the triazolidinedione compound represented by the formula (1).

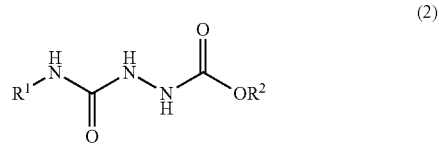

(2)

In the formula (2), $R^1$ is as defined in the formula (1), and $R^2$ represents an alkyl group having 1 to 20 carbon atoms and optionally containing an oxygen atom, an aralkyl group, or a substituted phenyl group.

Effects of the Invention

According to a method for producing a triazolidinedione compound of the present invention, crystals of a triazolidinedione compound can be obtained with high purity in high yields in an industrial manner.

PREFERRED MODE FOR CARRYING OUT THE INVENTION

<Method for Producing Triazolidinedione Compound>

A method for producing a triazolidinedione compound of the present invention includes a precipitation step of preparing a solution containing a triazolidinedione compound represented by the following formula (1), and precipitating the triazolidinedione compound. In this method, the pH of the solution prepared is adjusted to 3.0 to 8.5, and the solution contains a solvent in an amount of 3 to 15 parts by volume with respect to 1 part by mass of the triazolidinedione compound.

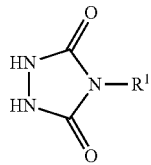

(1)

In the formula (1), $R^1$ represents an organic group including a substituted or unsubstituted amino group.

Furthermore, the method for producing a triazolidinedione compound of the present invention may include a cyclization step of reacting a semicarbazide compound represented by the following formula (2) with a base to obtain the triazolidinedione compound represented by the above formula (1). In the case where the cyclization step is included, the precipitation step described above is performed after the cyclization step.

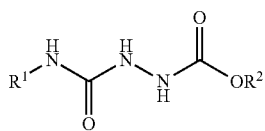

(2)

In the formula (2), $R^1$ is as defined in the formula (1), and $R^2$ represents an alkyl group having 1 to 20 carbon atoms and optionally containing an oxygen atom or a nitrogen atom, an aralkyl group, or a substituted phenyl group.

The triazolidinedione compound has a low solubility in water etc. within the aforementioned pH range. Thus, for example, adjusting the pH of the aqueous solution within the aforementioned range causes the triazolidinedione compound to precipitate. On the other hand, a semicarbazide compound which may be contained as an impurity has a higher solubility in water etc. within the aforementioned pH range. Therefore, in the method for producing a triazolidinedione compound of the present invention, by adjusting the pH of the solution prepared in the precipitation step within the range of 3.0 to 8.5, a highly pure triazolidinedione compound can be obtained.

With regard to the triazolidinedione compound, a higher chemical purity is more preferable in consideration of its storage. The chemical purity is preferably 90% or more, more preferably 95% or more, even more preferably 99.5% or more. Although the chemical purity of 100% is most preferable, the triazolidinedione compound obtained by the method for producing a triazolidinedione compound of the present invention may contain the semicarbazide compound represented by the above formula (2) which is a raw material, and/or hydrolyzates thereof.

[Triazolidinedione Compound]

The triazolidinedione compound used in the production method of the present invention has the structure represented by the above formula (1).

Herein, it is preferable that $R^1$ in the above formula (1) represents a substituted or unsubstituted aminoalkyl group having 1 to 6 carbon atoms, or a substituted or unsubstituted aminophenyl group or a substituted or unsubstituted aminoalkylphenyl group.

Among these, compounds having, as $R^1$, a group selected from the group consisting of a 3-dimethylaminopropyl group, a 4-dimethylaminophenyl group, or a 4-dimethylaminomethylphenyl group can be preferably used, and compounds having a 4-dimethylaminophenyl group or a 4-dimethylaminomethylphenyl group can be most preferably used in light of the availability of the raw materials and the stability.

[Cyclization Step]

In the case where the method for producing a triazolidinedione compound of the present invention includes the cyclization step, the semicarbazide compound represented by the above formula (2) is reacted with a base to obtain the triazolidinedione compound represented by the above formula (1). Specifically, the semicarbazide compound represented by the above formula (2) is brought into contact with the base in a solvent.

(Semicarbazide Compound)

As described above, $R^2$ in the above formula (2) represents an alkyl group having 1 to 20 carbon atoms and optionally containing an oxygen atom or a nitrogen atom, an aralkyl group, or a substituted phenyl group; among these, $R^2$ preferably represents an alkyl group having 1 to 4 carbon atoms in light of availability, price, and the like.

(Base)

The base which can be used in the cyclization step is not particularly limited. For example, inorganic bases such as sodium hydroxide, potassium hydroxide, sodium carbonate and potassium carbonate, and organic bases such as ammonia, triethylamine, diazabicyclo undecene (DBU), diazabicyclooctane (DABCO), pyridine and piperazine can be used. An inorganic base such as sodium hydroxide or potassium carbonate is preferably used, and potassium carbonate is most preferably used in light of production costs.

Although there is also no particular limitation on the amount of the base used in the cyclization step, the amount of the base is such an amount that the pH of the solvent falls preferably within the range of 9 to 14, more preferably within the range of 10 to 14, and most preferably within the range of 13 to 14 in light of the rate of reaction and the stability of the triazolidinedione compound, which is a product.

(Solvent)

The solvent used is particularly not limited as long as the product, i.e. the triazolidinedione compound and the base can be dissolved in the solvent, and the semicarbazide compound, which is a raw material, is not necessarily dissolved in the solvent. Examples of the solvent include: protic polar solvents such as water, methanol and ethanol; ether solvents such as diethyl ether, tetrahydrofuran and 1,2-dimethoxyethane; heteroatom-containing solvents such as N,N-dimethylformamide and N,N-dimethylacetamide; and the like. The aforementioned solvent may be used alone, or as a mixture of a plurality of types thereof. To produce a highly pure triazolidinedione compound, a protic polar solvent is preferably used, and water is most preferably used in light of costs.

(Method for Mixing Semicarbazide Compound, Base and Solvent)

A method for mixing the semicarbazide compound, the base and the solvent is not particularly limited, and can be performed, for example, in a reaction vessel equipped with a stirring apparatus. In addition, there is also no particular limitation on the order of adding each component into the reaction vessel. For example, after the semicarbazide compound is dissolved or suspended in the solvent, the base is added to cause the reaction. Alternatively, after the base is dissolved in the solvent, the semicarbazide compound may be added thereto. Although the semicarbazide compound and the base may be each added alone, they may be each dissolved in the solvent beforehand and then added.

(Reaction Conditions)

A temperature, i.e. reaction temperature (temperature in the reaction system) at which the semicarbazide compound and the base are mixed is not particularly limited. For example, the reaction temperature may be within the range of 60 to 100° C. In the present reaction, in order to complete the reaction within a short period of time while reducing impurities, the reaction temperature is preferably within the range of 70 to 100° C., and more preferably within the range of 80 to 100° C.

There is also no particular limitation on the reaction time, and typically, the reaction time in the range of 0.5 to 5 hours is sufficient, and the reaction time is within the range of preferably 0.5 to 3 hours, and more preferably 0.5 to 2 hours. Herein, the reaction time means a time period during which a total volume of the semicarbazide compound and the base is mixed. In addition, in the present invention, the reaction time may be determined while checking the reaction rate of the semicarbazide compound which is a raw material.

There is also no particular limitation on the reaction pressure, and the reaction may be performed either under atmospheric pressure, under reduced pressure, or under increased pressure. Moreover, there is also no particular limitation on the atmosphere during the reaction, and for example, the reaction may be performed under an air atmosphere, under an inert gas atmosphere, or the like. From the viewpoint of production costs, the reaction is preferably performed under an air atmosphere.

(Removal of Impurities)

The impurities may be removed after producing the triazolidinedione compound through the cyclization step and before performing the precipitation step. In the case where the impurities are precipitated as a solid after the completion of the cyclization step, the impurities can be removed by filtration. Alternatively, even when the impurities are not precipitated as a solid, the impurities can be removed by contacting the impurities with an organic solvent. The removal of the impurities contained in the triazolidinedione compound allows for an increase in the purity of the triazolidinedione compound finally obtained by the production method according to the present invention.

For the removal of the impurities, it is preferable to use an organic solvent immiscible with water in light of a removal efficiency. Examples of suitable organic solvents include: halogen-based solvents such as dichloromethane and chloroform; ester solvents such as ethyl acetate and butyl acetate; aromatic hydrocarbon solvents such as toluene, xylene and chlorobenzene; ether solvents such as diethyl ether and methyl t-butyl ether; and the like. Among these organic solvents, an organic solvent having a greater specific gravity than that of water is useful from the viewpoint of operability, since the organic solvent that contains the impurities can be removed from the bottom part of the reaction vessel. Such an organic solvent is exemplified by halogen-based solvents such as dichloromethane and chloroform.

[Precipitation Step]

In the precipitation step, the solution containing the triazolidinedione compound represented by the above formula (1) is prepared, and the triazolidinedione compound is caused to precipitate. In this step, the pH of the solution is adjusted to a range of 3.0 to 8.5, and the solution is prepared such that the solvent is contained in an amount of 3 to 15 parts by volume with respect to 1 part by mass of the triazolidinedione compound.

(pH of Solution)

The pH of the prepared solution is required to lie within the range of 3.0 to 8.5, and may be, for example, in the range of 4.5 to 8.5, in the range of 5.0 to 8.0, or in the range of 5.5 to 7.5. Alternatively, the pH of the solution may be in the range of 3.0 to 6.5, in the range of 3.5 to 6.0, or in the range of 4.0 to 5.5.

(Amount of Solution)

When the amount of the solution prepared is too small, the triazolidinedione compound is insufficiently dissolved, leading to a tendency for a lower purification effect, whereas an excessively large amount leads to a decrease in yield. The amount of the solvent is adjusted such that the solvent is contained in an amount in the range of 3 to 15 parts by volume, preferably in the range of 3 to 10 parts by volume, and particularly preferably in the range of 3 to 8 parts by volume with respect to 1 part by mass of the triazolidinedione compound.

(Method for Adjustment of pH)

A method for pH adjustment of the solution containing the triazolidinedione compound is not particularly limited, and the method for pH adjustment is exemplified by: a procedure in which the triazolidinedione compound is dissolved in water or the like, and then an acid is added to adjust the pH; and a procedure in which the triazolidinedione compound is dissolved in a basic aqueous solution, and then an acid is added to adjust the pH.

Further, the pH of the solution containing the triazolidinedione compound can be adjusted to the range of 3.0 to 6.5 by directly adding an acid to the reaction solution obtained in the cyclization step described above. In this case, the amount of the solution may be increased depending on the reaction condition, and in such a case, the amount of the solution may be adjusted to the aforementioned range by distilling off the solvent after the addition of the acid to adjust the pH. Alternatively, the solvent is distilled off after the completion of the reaction to achieve a predetermined proportion, and then the acid may be added to adjust the pH.

(Acid)

The acid used to adjust the pH is not particularly limited, and for example, an organic acid such as formic acid, acetic acid, propionic acid or oxalic acid, and an inorganic acid such as hydrochloric acid, sulfuric acid, nitric acid or phosphoric acid may be used. In addition, these acids may be used as an aqueous solution. Examples of the preferred acid include inorganic acids such as hydrochloric acid and sulfuric acid. Among these, hydrochloric acid is most preferably used in light of hydrochloric acid prices and ease in purification. In addition, with regard to the amount of the acid used, it is sufficient that the acid is added to the point where the solution containing the triazolidinedione compound reaches the desired pH.

Further, if the pH of the solution reaches a lower value than the pH necessary for the precipitation step, the pH can be adjusted to the pH range described above by adding a base. The base used is not particularly limited, and inorganic bases such as sodium hydroxide, sodium carbonate and potassium carbonate may be preferably used. Among these, potassium carbonate may be preferably used in light of ease in pH adjustment.

(Precipitation Conditions)

The temperature of the solution in the precipitation step is not particularly limited, and may be determined as appropriate in consideration of production conditions. From the viewpoint of the stability of the triazolidinedione compound, the range of 0 to 40° C. is preferable, the range of 10 to 30° C. is more preferable, and the range of 15 to 25° C. is most preferable.

There is also no particular limitation on the time period of the precipitation step, and the time period may be determined as appropriate in consideration of the production conditions and the like, and typically, a time period of about 30 minutes to 1 hour is sufficient.

The atmosphere in the precipitation step is not particularly limited, and the precipitation step may be performed, for example, either under an air atmosphere, under an inert gas atmosphere, or under a dry air atmosphere. Further, the precipitation step may be performed under any pressure such as under atmospheric pressure, under reduced pressure, or under increased pressure.

[Isolation of Triazolidinedione Compound]

According to the method for producing a triazolidinedione compound of the present invention, the triazolidinedione compound precipitates in the solution as a solid. Therefore, the triazolidinedione compound can be isolated using a known isolation procedure. Specifically, the suspension containing the triazolidinedione compound is subjected to solid-liquid separation using a procedure such as vacuum filtration, pressure filtration, or centrifugation, and thereby solids of the triazolidinedione compound can be isolated.

The solvent can be removed from the solids after the solid-liquid separation by drying the solids under ambient pressure, under reduced pressure, or under a flow of an inert gas such as nitrogen or argon. The drying temperature is preferably in the range of room temperature to 100° C. The drying time may be determined as appropriate while checking the amount of the residual solvent and the like, and typically falls within the range of 1 to 24 hours.

[Purification of Triazolidinedione Compound]

The triazolidinedione compound obtained by the method for producing a triazolidinedione compound of the present invention can be purified using a known method. For example, recrystallization using a protic or aprotic polar solvent (for example, methanol, ethanol, acetonitrile, acetone or the like) is preferable. The protic or aprotic polar solvent used for the recrystallization may contain water.

Although the temperature at which the triazolidinedione compound obtained by the method for producing a triazolidinedione compound of the present invention is dissolved in the recrystallization solvent is not particularly limited, the dissolution is performed at preferably in the range of 20 to 100° C., and more preferably in the range of 40 to 80° C.

The amount of the recrystallization solvent used is preferably 5 to 50 mL, and more preferably 5 to 20 mL with respect to 1 g of a target to be dissolved, i.e., the target containing the triazolidinedione compound. In addition, the temperature at which the crystals are precipitated is preferably in the range of 0 to 20° C., and more preferably in the range of 0 to 5° C. The obtained crystals can be dried using a known method.

EXAMPLES

Hereinafter, the embodiments of the present invention will be explained in more detail by way of Examples, but the present invention is not limited by these Examples.

<Chemical Purity Measurement (HPLC Purity)>

The purity measurement of a triazolidinedione compound in the present invention was performed using high performance liquid chromatography (HPLC) under the following conditions. The HPLC purity was calculated as area % of the triazolidinedione compound in the HPLC measurement.

(Measurement Conditions)

apparatus: high performance liquid chromatograph (2695 manufactured by Waters Corporation)

detector: ultraviolet-visible spectrometric detector (2489 manufactured by Waters Corporation)

detection wavelength: 210 nm column: Inertsil ODS-3 (4.6 mm×250 mm, particle size: 5 μm) (manufactured by GL Sciences Inc.)

mobile phase A: acetonitrile/buffer=5/95 mobile phase B: acetonitrile/buffer=30/70 buffer: prepared by dissolving 69.0 g of ammonium dihydrogenphosphate and 52.3 g of sodium 1-pentanesulfonate as an ion-pairing reagent in 3,000 mL of water, and adding hydrochloric acid to adjust the pH to 2.0 feeding of mobile phase: a concentration gradient was controlled by changing the profile as follows: mobile phase A (0 to 10 min)→mobile phase B (20 to 40 min).

column temperature: constant temperature close to 40° C.

injection volume: 10 μL sample concentration: 0.75 g/mL

Note that in the analysis by HPLC under the measurement conditions described above, a peak corresponding to the triazolidinedione compound appears at a retention time of about 9 min. In addition, peaks corresponding to impurities appear at retention times of 17 to 20 min.

Example 1

Synthesis of 1-Ethoxycarbonyl-4-(4'-Dimethylaminophenyl)Semicarbazide

To a 2-L four-necked glass flask, a mechanical stirrer, a thermometer, a Dimroth condenser and a gas inlet tube were attached. Into the flask, 100.00 g (0.61 mol) of 4-dimethylaminobenzoic acid and 1,000 mL of dehydrated toluene were charged, and the mixture was stirred under a nitrogen flow, to form a white slurry.

When 73.51 g (0.73 mol) of triethylamine, and 199.92 g (0.73 mol) of diphenylphosphoryl azide were added to the white slurry, the temperature inside the system increased to 33° C., and a light yellow transparent solution was formed. The flask was heated by placing the flask in an oil bath (100° C.), and the reaction was caused for 1 hour with the temperature inside the system being 90 to 100° C. Evolution of nitrogen gas was observed at a temperature inside the system of about 70° C. or higher, and a dark orange solution was formed.

The flask was removed from the oil bath and allowed to cool. After the temperature inside the system reached about 40° C., 75.63 g (0.73 mol) of ethyl carbazate was added. The temperature inside the system increased to 53° C., and a bilayer orange solution was formed. After the reaction was caused for 1 hour, the reaction mixture was transferred to a 5-L Erlenmeyer flask, 2,000 mL of distilled water was added, and the mixture was stirred with a mechanical stirrer for 3 hours.

The reaction mixture was filtered through a Kiriyama funnel (No. 5B), followed by washing with 400 mL of distilled water and 400 mL of toluene, to obtain a beige solid. The obtained solid was vacuum dried (40° C., 12 hours), to obtain 1-ethoxycarbonyl-4-(4'-dimethylaminophenyl)semicarbazide as a beige solid. The amount of the product was 141.96 g, the yield was 88.1%, and the HPLC purity was 88.4%.

Synthesis of 4-(4'-Dimethylaminophenyl)-1,2,4-Triazolidine-3,5-Dione

To a 300-mL four-necked glass flask, a mechanical stirrer, a thermometer and a Dimroth condenser were attached. Into the flask, 10.00 g (37.6 mmol) of 1-ethoxycarbonyl-4-(4'-dimethylaminophenyl)semicarbazide obtained as described above, 10.00 g (72.4 mmol) of potassium carbonate (anhydrous), and 200 mL of distilled water were charged, and the mixture was stirred. At that point, the semicarbazide was not dissolved, but was suspended. The flask was heated by placing the flask in an oil bath (110° C.), and the reaction was caused for 2 hours with the temperature inside the system being 95° C. During the reaction, the reaction mixture changed to a yellow suspension.
(pH Adjustment)

The flask was removed from the oil bath and allowed to cool, and filtration through filter paper (No. 2) was conducted to remove insolubles. Subsequently, water was distilled off with an evaporator to concentrate the filtrate to about 50 g (50 mL). The concentrated solution was transferred to a conical beaker, and pH adjustment was conducted by adding concentrated hydrochloric acid with a burette. When 11.7 mL of concentrated hydrochloric acid was added dropwise (pH=4.79), the pH adjustment was completed. In this synthesis, the amount of the solvent with respect to 1 part by mass (theoretical amount of the product) of the triazolidine compound was 6.5 parts by volume.

The slurry obtained thus was filtered through a Kiriyama funnel (No. 5B), followed by washing with 50 mL of distilled water. The obtained solid was vacuum dried (40° C., 12 hours), to obtain 4-(4'-dimethylaminophenyl)-1,2,4-triazolidine-3,5-dione as a white solid. The amount of the product was 6.77 g, the yield was 81.9%, and the HPLC purity was 98.5%.

Example 2

Synthesis of 1-Ethoxycarbonyl-4-(2-Dimethylaminoethyl)Semicarbazide

To a 2-L four-necked glass flask, a mechanical stirrer, a thermometer, a Dimroth condenser and a gas inlet tube were attached. Into the flask, 92.99 g (0.61 mol) of 3-dimethylaminopropionic acid hydrochloride and 1,000 mL of dehydrated toluene were charged, and the mixture was stirred under a nitrogen flow, to form a white slurry.

When 147.02 g (1.46 mol) of triethylamine, and 199.92 g (0.73 mol) of diphenylphosphoryl azide were added to the white slurry, the temperature inside the system increased to 40° C., and a light yellow transparent solution was formed. The flask was heated by placing the flask in an oil bath (100° C.), and the reaction was caused for 1 hour with the temperature inside the system being 90 to 100° C. Evolution of nitrogen gas was observed at a temperature inside the system of about 70° C. or higher, and a dark orange solution was formed.

The flask was removed from the oil bath and allowed to cool. After the temperature inside the system reached about 40° C., 75.63 g (0.73 mol) of ethyl carbazate was added. The temperature inside the system increased to 47° C., and a bilayer orange solution was formed. After the reaction was caused for 1 hour, the reaction mixture was transferred to a 5-L Erlenmeyer flask, 2,000 mL of distilled water was added, and the mixture was stirred with a mechanical stirrer for 3 hours.

The reaction mixture was filtered through a Kiriyama funnel (No. 5B), followed by washing with 400 mL of distilled water and 400 mL of toluene, to obtain a beige solid. The obtained solid was vacuum dried (40° C., 12 hours), to obtain 1 ethoxycarbonyl-4-(2-dimethylaminoethyl)semicarbazide as a beige solid. The amount of the product was 120.65 g, the yield was 85.8%, and the HPLC purity was 86.1%.

Synthesis of 4-(2Dimethylaminoethyl)-1,2,4-Triazolidine-3,5-Dione

To a 300-mL four-necked glass flask, a mechanical stirrer, a thermometer and a Dimroth condenser were attached. Into the flask, 8.73 g (37.6 mmol) of 1 ethoxycarbonyl-4-(2-dimethylaminoethyl)semicarbazide obtained as described above, 10.00 g (72.4 mmol) of potassium carbonate (anhydrous), and 200 mL of distilled water were charged, and the mixture was stirred. At that point, the semicarbazide was not dissolved, but was suspended. The flask was heated by placing the flask in an oil bath (110° C.), and the reaction was caused for 2 hours with the temperature inside the system being 95° C. During the reaction, the reaction mixture was changed to a yellow suspension.
(pH Adjustment)

The flask was removed from the oil bath and allowed to cool, and filtration through filter paper (No. 2) was conducted to remove insolubles. Subsequently, water was distilled off with an evaporator to concentrate the filtrate to about 50 g (50 mL). The concentrated solution was transferred to a conical beaker, and pH adjustment was conducted by adding concentrated hydrochloric acid with a burette. When 11.5 mL of concentrated hydrochloric acid was added dropwise (pH=6.01), the pH adjustment was completed. In this synthesis, the amount of the solvent with respect to 1 part by mass (theoretical amount of the product) of the triazolidine compound was 7.8 parts by volume.

The slurry obtained thus was filtered through a Kiriyama funnel (No. 5B), followed by washing with 50 mL of distilled water. The obtained solid was vacuum dried (40° C., 12 hours), to obtain 4-(2 dimethylaminoethyl)-1,2,4-triazolidine-3,5-dione as a white solid. The amount of the product was 8.27 g, the yield was 84.6%, and the HPLC purity was 98.1%.

Example 3

Synthesis of 1-Ethoxycarbonyl-4-(3-Dimethylaminopropyl)Semicarbazide

To a 2-L four-necked glass flask, a mechanical stirrer, a thermometer, a Dimroth condenser and a gas inlet tube were attached. Into the flask, 101.48 g (0.61 mol) of 4-dimethylaminobutyric acid hydrochloride and 1,000 mL of dehydrated toluene were charged, and the mixture was stirred under a nitrogen flow, to form a white slurry. When 147.02 g (1.46 mol) of triethylamine, and 199.92 g (0.73 mol) of diphenylphosphoryl azide were added to the white slurry, the temperature inside the system increased to 40° C., and a light yellow transparent solution was formed. The flask was heated by placing the flask in an oil bath (100° C.), and the reaction was caused for 1 hour with the temperature inside the system being 90 to 100° C. Evolution of nitrogen gas was observed at a temperature inside the system of about 70° C. or higher, and a dark orange solution was formed.

The flask was removed from the oil bath and allowed to cool. After the temperature inside the system reached about 40° C., 75.63 g (0.73 mol) of ethyl carbazate was added. The temperature inside the system increased to 47° C., and a bilayer orange solution was formed. After the reaction was caused for 1 hour, the reaction mixture was transferred to a 5-L Erlenmeyer flask, 2,000 mL of distilled water was added, and the mixture was stirred with a mechanical stirrer for 3 hours.

The reaction mixture was filtered through a Kiriyama funnel (No. 5B), followed by washing with 400 mL of distilled water and 400 mL of toluene, to obtain a beige solid. The obtained solid was vacuum dried (40° C., 12 hours), to obtain 1-ethoxycarbonyl-4-(3-dimethylaminopropyl)semicarbazide as a beige solid. The amount of the product was 120.65 g, the yield was 85.8%, and the HPLC purity was 86.1%.

Synthesis of 4-(3-Dimethylaminopropyl)-1,2,4-Triazolidine-3,5-Dione

To a 300-mL four-necked glass flask, a mechanical stirrer, a thermometer and a Dimroth condenser were attached. Into the flask, 8.73 g (37.6 mmol) of 1-ethoxycarbonyl-4-(3-dimethylaminopropyl)semicarbazide obtained as described above, 10.00 g (72.4 mmol) of potassium carbonate (anhydrous), and 200 mL of distilled water were charged, and the mixture was stirred. At that point, the semicarbazide was not dissolved, but was suspended. The flask was heated by placing the flask in an oil bath (110° C.), and the reaction was caused for 2 hours with the temperature inside the system being 95° C. During the reaction, the reaction mixture was changed to a yellow suspension.
(pH Adjustment)

The flask was removed from the oil bath and allowed to cool, and filtration through filter paper (No. 2) was conducted to remove insolubles. Subsequently, water was distilled off with an evaporator to concentrate the filtrate to about 50 g (50 mL). The concentrated solution was transferred to a conical beaker, and pH adjustment was conducted by adding concentrated hydrochloric acid with a burette. When 11.5 mL of concentrated hydrochloric acid was added dropwise (pH=6.01), the pH adjustment was completed. In this synthesis, the amount of the solvent with respect to 1 part by mass (theoretical amount of the product) of the triazolidine compound was 7.8 parts by volume.

The slurry obtained thus was filtered through a Kiriyama funnel (No. 5B), followed by washing with 50 mL of distilled water. The obtained solid was vacuum dried (40° C., 12 hours), to obtain 4-(3-dimethylaminopropyl)-1,2,4-triazolidine-3,5-dione as a white solid. The amount of the product was 5.02 g, the yield was 71.7%, and the HPLC purity was 97.7%.

Example 4

Synthesis of 1-Ethoxycarbonyl-4-(3-Dimethylaminopropyl)Semicarbazide

To a 2-L four-necked glass flask, a mechanical stirrer, a thermometer, a Dimroth condenser and a gas inlet tube were attached. Into the flask, 101.48 g (0.61 mol) of 4-dimethylaminobutyric acid hydrochloride and 1,000 mL of dehydrated toluene were charged, and the mixture was stirred under a nitrogen flow, to form a white slurry.

When 147.02 g (1.46 mol) of triethylamine, and 199.92 g (0.73 mol) of diphenylphosphoryl azide were added to the white slurry, the temperature inside the system increased to 40° C., and a light yellow transparent solution was formed.

The flask was heated by placing the flask in an oil bath (100° C.), and the reaction was caused for 1 hour with the temperature inside the system being 90 to 100° C. Evolution of nitrogen gas was observed at a temperature inside the system of about 70° C. or higher, and a dark orange solution was formed.

The flask was removed from the oil bath and allowed to cool. After the temperature inside the system reached about 40° C., 75.63 g (0.73 mol) of ethyl carbazate was added. The temperature inside the system increased to 47° C., and a bilayer orange solution was formed. After the reaction was caused for 1 hour, the reaction mixture was transferred to a 5-L Erlenmeyer flask, 2,000 mL of distilled water was added, and the mixture was stirred with a mechanical stirrer for 3 hours.

The reaction mixture was filtered through a Kiriyama funnel (No. 5B), followed by washing with 400 mL of distilled water and 400 mL of toluene, to obtain a beige solid. The obtained solid was vacuum dried (40° C., 12 hours), to obtain 1-ethoxycarbonyl-4-(3-dimethylaminopropyl)semicarbazide as a beige solid. The amount of the product was 120.65 g, the yield was 85.8%, and the HPLC purity was 86.1%.

Synthesis of 4-(3-Dimethylaminopropyl)-1,2,4-Triazolidine-3,5-Dione

To a 300-mL four-necked glass flask, a mechanical stirrer, a thermometer and a Dimroth condenser were attached. Into the flask, 8.73 g (37.6 mmol) of 1-ethoxycarbonyl-4-(3-dimethylaminopropyl)semicarbazide obtained as described above, 10.00 g (72.4 mmol) of potassium carbonate (anhydrous), and 200 mL of distilled water were charged, and the mixture was stirred. At that point, the semicarbazide was not dissolved, but was suspended. The flask was heated by placing the flask in an oil bath (110° C.), and the reaction was caused for 2 hours with the temperature inside the system being 95° C. During the reaction, the reaction mixture was changed to a yellow suspension.
(pH Adjustment)

The flask was removed from the oil bath and allowed to cool, and filtration through filter paper (No. 2) was conducted to remove insolubles. Subsequently, water was distilled off with an evaporator to concentrate the filtrate to about 50 g (50 mL). The concentrated solution was transferred to a conical beaker, and pH adjustment was conducted by adding concentrated hydrochloric acid with a burette. When 4.8 mL of concentrated hydrochloric acid was added dropwise (pH=7.46), the pH adjustment was completed. In this synthesis, the amount of the solvent with respect to 1 part by mass (theoretical amount of the product) of the triazolidine compound was 6.8 parts by volume.

The slurry obtained thus was filtered through a Kiriyama funnel (No. 5B), followed by washing with 50 mL of distilled water. The obtained solid was vacuum dried (40° C., 12 hours), to obtain 4-(3-dimethylaminopropyl)-1,2,4-triazolidine-3,5-dione as a white solid. The amount of the product was 5.92 g, the yield was 84.6%, and the HPLC purity was 98.1%.

Example 5

Synthesis of 1-Ethoxycarbonyl-4-(4'-Dimethylaminomethylphenyl)Semicarbazide To a 2-L four-necked glass flask, a mechanical stirrer, a thermometer, a Dimroth condenser and a gas inlet tube were attached. Into the flask, 109.32 g (0.61 mol) of 4-dimethylaminomethylbenzoic acid, and 1,000 mL of dehydrated toluene were charged, and the mixture was stirred under a nitrogen flow, to form a white slurry.

When 73.51 g (0.73 mol) of triethylamine, and 199.92 g (0.73 mol) of diphenylphosphoryl azide were added to the white slurry, the temperature inside the system increased to 30° C., and a light yellow transparent solution was formed. The flask was heated by placing the flask in an oil bath (100° C.), and the reaction was caused for 1 hour with the temperature inside the system being 90 to 100° C. Evolution of nitrogen gas was observed at a temperature inside the system of about 70° C. or higher, and a dark orange solution was formed.

The flask was removed from the oil bath and allowed to cool. After the temperature inside the system reached about 40° C., 75.63 g (0.73 mol) of ethyl carbazate was added. The temperature inside the system increased to 46° C., and a bilayer orange solution was formed. After the reaction was caused for 1 hour, the reaction mixture was transferred to a 5-L Erlenmeyer flask, 2,000 mL of distilled water was added, and the mixture was stirred with a mechanical stirrer for 3 hours.

The reaction mixture was filtered through a Kiriyama funnel (No. 5B), followed by washing with 400 mL of distilled water and 400 mL of toluene, to obtain a beige solid. The obtained solid was vacuum dried (40° C., 12 hours), to obtain 1-ethoxycarbonyl-4-(4'-dimethylaminomethylphenyl)semicarbazide as a beige solid. The amount of the product was 123.32 g, the yield was 86.3%, and the HPLC purity was 89.6%.

Synthesis of 4-(4'-Dimethylaminomethylphenyl)-1,2,4-Triazolidine-3,5-Dione

To a 300-mL four-necked glass flask, a mechanical stirrer, a thermometer and a Dimroth condenser were attached. Into the flask, 10.54 g (37.6 mmol) of 1-ethoxycarbonyl-4-(4'-dimethylaminomethylphenyl) semicarbazide obtained as described above, 10.00 g (72.4 mmol) of potassium carbonate (anhydrous), and 200 mL of distilled water were charged, and the mixture was stirred. At that point, the semicarbazide was not dissolved, but was suspended. The flask was heated by placing the flask in an oil bath (110° C.), and the reaction was caused for 2 hours with the temperature inside the system being 95° C. During the reaction, the reaction mixture was changed to a yellow suspension.
(pH Adjustment)

The flask was removed from the oil bath and allowed to cool, and filtration through filter paper (No. 2) was conducted to remove insolubles. Subsequently, water was distilled off with an evaporator to concentrate the filtrate to about 50 g (50 mL). The concentrated solution was transferred to a conical beaker, and pH adjustment was conducted by adding concentrated hydrochloric acid with a burette. When 10.7 mL of concentrated hydrochloric acid was added dropwise (pH=6.68), the pH adjustment was completed. In this synthesis, the amount of the solvent with respect to 1 part by mass (theoretical amount of the product) of the triazolidine compound was 5.9 parts by volume.

The slurry obtained thus was filtered through a Kiriyama funnel (No. 5B), followed by washing with 50 mL of distilled water. The obtained solid was vacuum dried (40° C., 12 hours), to obtain 4-(4'-dimethylaminomethylphenyl)-1,2,4-triazolidine-3,5-dione as a white solid. The amount of the product was 7.34 g, the yield was 83.3%, and the HPLC purity was 98.3%.

Comparative Example 1

Synthesis of 4-(4'-dimethylaminophenyl)-1,2,4-triazolidine-3,5-dione was conducted in the same manner as Example 1 except that the amount of concentrated hydrochloric acid added in the pH adjustment was changed to 13.0 mL. Consequently, the pH was 2.70, the amount of 4-[4-(dimethylamino)phenyl]-1,2,4-triazolidine-3,5-dione obtained thus was 5.54 g, the yield was 67.0%, and the HPLC purity was 98.1%. In this synthesis, the amount of the solvent with respect to 1 part by mass (theoretical amount of the product) of the triazolidine compound was 6.6 parts by volume.

Comparative Example 2

A solution containing 4-(4'-(dimethylaminophenyl)-1,2,4-triazolidine-3,5-dione was prepared in the same manner as Example 1 except that the distillation of water with the evaporator was not conducted, and 11.7 mL of concentrated hydrochloric acid was added (pH=4.79). The amount of 4-(4'-dimethylaminophenyl)-1,2,4-triazolidine-3,5-dione obtained was 1.61 g, the yield was 19.5%, and the HPLC purity was 97.3%. In this synthesis, the amount of the solvent with respect to 1 part by mass (theoretical amount of the product) of the triazolidine compound was 26.3 parts by volume.

The invention claimed is:

1. A method for producing a triazolidinedione compound, comprising a precipitation step of preparing an aqueous solution comprising a triazolidinedione compound represented by formula (1), and precipitating the triazolidinedione compound by an isoelectric point precipitation method, wherein a pH of the aqueous solution is 3.0 to 8.5, and the aqueous solution comprises a solvent in an amount of 3 to 15 parts by volume with respect to 1 part by mass of the triazolidinedione compound, the method further comprising a cyclization step of reacting a semicarbazide compound represented by formula (2) with a base to obtain the triazolidinedione compound represented by the formula (1):

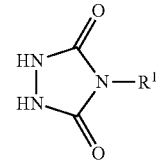

(1)

wherein in the formula (1), $R^1$ represents a substituted or unsubstituted aminoalkyl group having 1 to 6 carbon atoms, or a substituted or unsubstituted aminophenyl group or a substituted or unsubstituted aminoalkylphenyl group, the formula (2) being
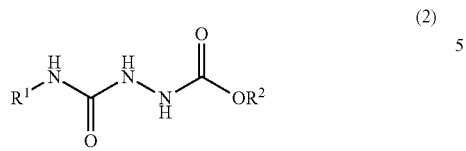
(2)
wherein in the formula (2), $R^1$ is as defined in the formula (1), and $R^2$ represents an alkyl group having 1 to 20 carbon atoms and optionally comprising an oxygen atom or a nitrogen atom, an aralkyl group, or a substituted phenyl group.
* * * * *

UNITED STATES PATENT AND TRADEMARK OFFICE
CERTIFICATE OF CORRECTION

| | |
|---|---|
| PATENT NO. | : 11,339,133 B2 |
| APPLICATION NO. | : 16/973216 |
| DATED | : May 24, 2022 |
| INVENTOR(S) | : Satou et al. |

It is certified that error appears in the above-identified patent and that said Letters Patent is hereby corrected as shown below:

On the Title Page

Item (73), Please change the Assignees to read as follows:
TOKUYAMA CORPORATION, Yamaguchi (JP); JEOL LTD., Tokyo (JP)

Signed and Sealed this
Thirteenth Day of September, 2022

Katherine Kelly Vidal
*Director of the United States Patent and Trademark Office*